US009822010B2

(12) United States Patent
Traynor et al.

(10) Patent No.: US 9,822,010 B2
(45) Date of Patent: *Nov. 21, 2017

(54) CERAMIC ENCAPSULATION BY USE OF ONE OR MORE SPECIALIZED SILANES TO TEMPLATE OIL IN AN OIL IN WATER EMULSION

(75) Inventors: Daniel H. Traynor, Sarasota, FL (US); Hao Xu, Canton, MI (US); Henry G. Traynor, Sarasota, FL (US); John Carson, Union City, NJ (US); Martin S. Flacks, Danville, CA (US)

(73) Assignee: CoLabs International Corporation, Las Vegas, NV (US)

( * ) Notice: Subject to any disclaimer, the term of this patent is extended or adjusted under 35 U.S.C. 154(b) by 419 days.

This patent is subject to a terminal disclaimer.

(21) Appl. No.: 13/011,564

(22) Filed: Jan. 21, 2011

(65) Prior Publication Data

US 2011/0256304 A1    Oct. 20, 2011

Related U.S. Application Data

(60) Provisional application No. 61/297,122, filed on Jan. 21, 2010.

(51) Int. Cl.
*B05D 3/10* (2006.01)
*C01B 33/18* (2006.01)
(Continued)

(52) U.S. Cl.
CPC ............... *C01B 33/18* (2013.01); *C09C 1/30* (2013.01); *A61K 9/501* (2013.01);
(Continued)

(58) Field of Classification Search
USPC ........ 427/212, 2.14; 428/402, 402.2, 402.24, 428/403; 424/408, 401, 400
See application file for complete search history.

(56) References Cited

U.S. PATENT DOCUMENTS

| 5,126,061 A | 6/1992 | Michael |
| 5,387,622 A | 2/1995 | Yamamoto |

(Continued)

FOREIGN PATENT DOCUMENTS

BE    WO 03066209 A1 *    8/2003    ............... A61K 8/11

OTHER PUBLICATIONS

Currie, "Use of Self-assembled Surfactant Systems as Media for a Substitution Reaction", Chalmers University of Technology, Department of Materials and Surface Chemistry, Goteborg, Sweden, Journal of Colloid and Interface Science, Apr. 20, 2004, p. 230-234.*

(Continued)

*Primary Examiner* — Alexander M Weddle
(74) *Attorney, Agent, or Firm* — UltimatEdge IP Law Group, P.C.; Dean G. Stathakis

(57) ABSTRACT

This invention relates to a method for emulsion templating hollow silica-based particles. The particles are suitable for containing one or more active ingredients or for containing other smaller particles which may include one or more active ingredients. The emulsion templated particles can be formed from two or more silanes. The emulsion templated particles can also be formed from a silane and a compound that attaches a polymer on the shell of the hollow silica-based particles.

19 Claims, 3 Drawing Sheets

(51) Int. Cl.
  *C09C 1/30*  (2006.01)
  *A61K 9/50*  (2006.01)

(52) U.S. Cl.
  CPC ...... *C01P 2004/03* (2013.01); *C01P 2004/34* (2013.01); *C01P 2004/52* (2013.01)

(56) References Cited

U.S. PATENT DOCUMENTS

| | | |
|---|---|---|
| 6,251,313 B1 | 6/2001 | Deubzer et al. |
| 6,303,149 B1* | 10/2001 | Magdassi et al. ............ 424/489 |
| 6,468,509 B2 | 10/2002 | Lapidot et al. |
| 6,855,335 B2 | 2/2005 | Seok et al. |
| 6,998,113 B1 | 2/2006 | Traynor et al. |
| 7,001,592 B1 | 2/2006 | Traynor et al. |
| 7,025,952 B1 | 4/2006 | Traynor et al. |
| 7,037,513 B1 | 5/2006 | Traynor et al. |
| 7,153,525 B1 | 12/2006 | Mumper et al. |
| 7,217,762 B1* | 5/2007 | Jorgedal et al. ............ 524/800 |
| 7,226,581 B2 | 6/2007 | Traynor et al. |
| 7,226,582 B2 | 6/2007 | Traynor et al. |
| 7,563,451 B2 | 7/2009 | Lin et al. |
| 2002/0064541 A1* | 5/2002 | Lapidot et al. ............ 424/401 |
| 2003/0157330 A1 | 8/2003 | Ostafin et al. |
| 2004/0091411 A1 | 5/2004 | Modrek-Najafabadi |
| 2005/0059748 A1* | 3/2005 | Blankenship ............ 521/50 |
| 2006/0018966 A1 | 1/2006 | Lin et al. |
| 2006/0155376 A1* | 7/2006 | Asgari ............ 623/16.11 |
| 2006/0167147 A1 | 7/2006 | Asgari |
| 2006/0173709 A1 | 8/2006 | Traynor et al. |
| 2006/0292345 A1 | 12/2006 | Dave et al. |
| 2007/0036736 A1* | 2/2007 | Kalla et al. ............ 424/63 |
| 2007/0292676 A1* | 12/2007 | Naigertsik et al. ........ 428/321.5 |
| 2008/0112904 A1 | 5/2008 | Traynor et al. |
| 2008/0199523 A1* | 8/2008 | Finnie et al. ............ 424/484 |
| 2008/0233509 A1 | 9/2008 | Keoshkerian et al. |
| 2008/0317795 A1* | 12/2008 | Traynor et al. ............ 424/401 |
| 2010/0016200 A1 | 1/2010 | Nagare et al. |
| 2010/0143422 A1 | 6/2010 | Popplewell et al. |
| 2010/0247660 A1 | 9/2010 | Lei et al. |

OTHER PUBLICATIONS

Biology Online, "Polar Molecule", http://www.biology-online.org/dictionary/Polar_molecule.*

Transtutors.com, "Emulsion", http://www.transtutors.com/chemistry-homework-help/surface-chemistry/emulsion.aspx.*

* cited by examiner

CERAMIC ENCAPSULATION BY USE OF ONE OR MORE SPECIALIZED SILANES TO TEMPLATE OIL IN AN OIL IN WATER EMULSION

CROSS-REFERENCES TO RELATED APPLICATIONS

This application claims priority from U.S. Patent Application No. 61/297,122 filed Jan. 21, 2010.

STATEMENT REGARDING FEDERALLY SPONSORED RESEARCH

Not Applicable.

BACKGROUND OF THE INVENTION

1. Field of the Invention

This invention relates to a method for forming hollow silica-based particles suitable for containing one or more active ingredients or for containing other smaller particles which can include one or more active ingredients.

2. Description of the Related Art

One approach to providing an active ingredient to a surface, such as the skin, is to encapsulate the active ingredient in order to protect the active ingredient, control the release of the active ingredient, and/or modify the function of the active ingredient. Methods for encapsulation of an active ingredient, such as sol-gel encapsulation, are known in the art. See, for example U.S. Patent Application Publication No. 2008/0317795 to Traynor et al.

Even with the advances in the art described in U.S. 2008/0317795, there is still a need for further improved encapsulation techniques.

SUMMARY OF THE INVENTION

The present invention provides an oil in water emulsion for forming silica-based particles that encapsulate one or more active ingredients or encapsulate other smaller particles which can include one or more active ingredients. The oil in water emulsion includes an aqueous continuous phase; a dispersed phase comprising droplets including a non-polar material and/or one or more oils; and two different silica precursors, wherein the silica precursors can be templated on the droplets to form the silica-based particles. The present invention also provides a templated silica particle formed from the oil in water emulsion of the invention wherein the silica particle can be modified from a continuously formed shell to a partially formed hollow shell by adjusting a ratio of the two silica precursors in the emulsion.

The present invention also provides an oil in water emulsion for making silica-based particles. The emulsion includes an aqueous continuous phase; a dispersed phase comprising droplets including a non-polar material; and an organically modified silica precursor with at least one carbon, wherein the silica precursor can be templated on the droplets to make the silica-based particles.

The present invention also provides an oil-in-water emulsion system for making silica coated particles. The emulsion includes an aqueous continuous phase; a surfactant component comprising a surfactant selected from anionic surfactants, nonionic surfactants, cationic surfactants, nonionic surfactants, and mixtures thereof, each surfactant in the surfactant component being at or below a critical micelle concentration of each surfactant; a dispersed phase comprising one or more non-polar materials that are incompatible with the aqueous phase and form droplets; a first organically modified silica precursor having a carbon atom and having a first functional group that is capable of further reaction, and a second organically modified silica precursor having a carbon atom that is combined with the first organically modified silica precursor and having a second functional group, wherein the carbon atom of the second precursor and the second functional group are in a ratio from 1 to 99 to 99 to 1, and wherein the first organically modified silica precursor and the second organically modified silica precursor can be reacted to form precipitated silica shells around the droplets which act as templates.

The present invention also provides a method for forming hollow silica-based particles. The method includes (a) preparing an emulsion including a continuous phase that is polar, and a dispersed phase comprising droplets including a non-polar active ingredient; (b) adding a first silica precursor to the emulsion such that the first silica precursor is emulsion templated on the droplets to form hollow silica-based particles having a shell and a core including the non-polar active ingredient, wherein the first silica precursor has the general formula (I):

$$R^1{}_x\text{—Si—}(OR^2)_y \quad (I)$$

wherein $R^1$ is selected from substituted and unsubstituted alkyl, aryl, alcohols, amines, amides, aldehydes, acids, esters, and functional groups having an unsaturated carbon-carbon bond, wherein $R^2$ is an alkyl group, wherein $x+y=4$, and wherein $x=0$ or 1 or 2; and (c) adding a second precursor to the emulsion such that a coating can be deposited on at least part of the shell of the hollow silica-based particles.

In one example embodiment, the invention provides a method for forming hollow silica-based particles. In this method, an emulsion is prepared that includes a continuous phase that is polar, and a dispersed phase comprising droplets including a non-polar active ingredient. A first silica precursor is added to the emulsion such that the first silica precursor is emulsion templated on the droplets to form hollow silica-based particles having a shell and a core including the non-polar active ingredient. In one form, the first silica precursor has the general formula (I):

$$R^1{}_x\text{—Si—}(OR^2)_y \quad (I)$$

wherein $R^1$ is selected from substituted and unsubstituted alkyl, aryl, alcohols, amines, amides, aldehydes, acids, esters, and functional groups having an unsaturated carbon-carbon bond, wherein $R^2$ is an alkyl group, wherein $x+y=4$, and wherein $x=0$ or 1 or 2. A second silica precursor is added to the emulsion such that the second silica precursor can be deposited on the shell of the hollow silica-based particles. In one form, the second silica precursor has the general formula (II):

$$R^3{}_m\text{—Si—}(OR^4)_n \quad (II)$$

wherein $R^3$ is selected from substituted and unsubstituted alkyl, aryl, alcohols, amines, amides, aldehydes, acids, esters, and functional groups having an unsaturated carbon-carbon bond, and amino functional groups, wherein $R^4$ is an alkyl group, wherein $m+n=4$, and wherein $m=0$, 1, or 2. Optionally, a third silica precursor can be added to the emulsion such that the third silica precursor can be emulsion templated on the droplets or deposited on the hollow silica-based particles to form hollow silica-based particles. The third silica precursor has the general formula (III):

$$R^5{}_a\text{—Si—}(OR^6)_b \quad (III)$$

wherein R⁵ is selected from substituted and unsubstituted alkyl, substituted and unsubstituted aryl, functional groups having an unsaturated carbon-carbon bond, functional groups having a carboxylic acid group, polymers of alkylene oxide, and amino functional groups, R⁶ is an alkyl group, a+b=4, and a=0, 1, 2 or 3. In this method, at least one of R¹ and R³ is preferably selected from phenyl, C₁₂-C₂₄ alkyl, substituted or unsubstituted acrylic acid, alkylamine, alkyl carboxylate, and alkyl quaternary amine.

In another example embodiment, the invention provides a method for forming hollow silica-based particles. In the method, an emulsion is prepared that includes a continuous phase that is polar, and a dispersed phase comprising droplets including a non-polar active ingredient. A silica precursor is added to the emulsion such that the silica precursor is emulsion templated on the droplets to form hollow silica-based particles having a shell and a core including the non-polar active ingredient. In one form, the silica precursor has the general formula (I):

$$R^1{}_x\text{—Si—}(OR^2)_y \quad (I)$$

wherein R¹ is selected from substituted and unsubstituted alkyl, aryl, alcohols, amines, amides, aldehydes, acids, esters, and functional groups having an unsaturated carbon-carbon bond, wherein R² is an alkyl group, wherein x+y=4, and wherein x=0 or 1 or 2. A compound is added to the emulsion such that a polymer is attached on the shell of the hollow silica-based particles. The polymer may be charged. In one form, the compound is an unsaturated compound, or a water soluble polymerizable compound. In this method, R¹ is preferably selected from phenyl, C₁₂-C₂₄ alkyl, substituted or unsubstituted acrylic acid, alkylamine, alkyl carboxylate, and alkyl quaternary amine.

It is an advantage of the invention to provide a method for encapsulation of an active ingredient in hollow silica-based particles in which unencapsulated particles formed in the method are minimized.

It is another advantage of the invention to provide a method for encapsulation of an active ingredient in hollow silica-based particles in which the particles do not need to be post-loaded with the active ingredient.

It is another advantage of the invention to provide a method for encapsulation of an active ingredient in hollow silica-based particles in which the reaction time is minimized in relation to other encapsulation methods.

It is another advantage of the invention to provide a method for encapsulation of an active ingredient in hollow silica-based particles in which Stöber (unencapsulated) particles are minimized.

It is another advantage of the invention to provide a method for encapsulation of an active ingredient in hollow silica-based particles in which the resulting particles do not become brittle when dried.

It is another advantage of the invention to provide a method for encapsulation of an active ingredient in hollow silica-based particles in which the particles have a surface functionality or a chargeable surface for attachment of additional molecules.

These and other features, aspects, and advantages of the present invention will become better understood upon consideration of the following detailed description, drawings and appended claims.

DETAILED DESCRIPTION OF THE INVENTION

Figure 1:
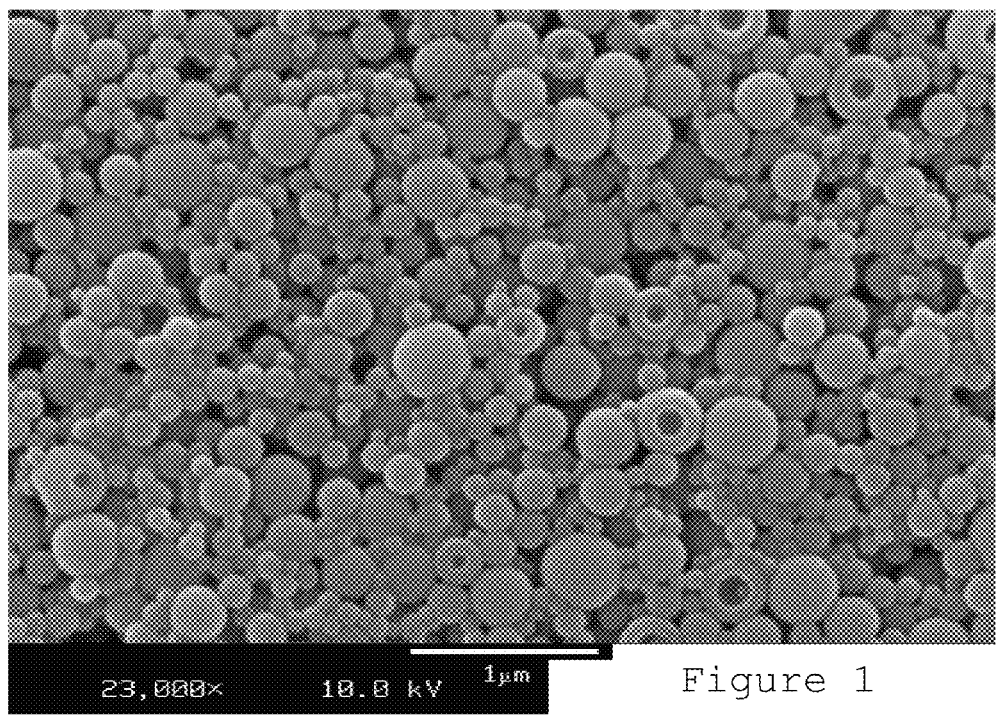
FIG. 1 is a scanning electron microscope (SEM) image of silica-based particles formed using a method of the invention.

The invention provides a method of forming silica-based particles including a non-polar active ingredient. In the method, a non-polar active ingredient, a surfactant, and water are combined and agitated to form an oil-in-water emulsion wherein the non-polar active ingredient and any optional non-polar diluent comprise a dispersed phase in the aqueous continuous phase. Silica precursors are added to the oil-in-water emulsion and mixed. The silica precursors hydrolyze and silica-based particles are formed which include the non-polar active ingredient. Two or more different silica precursors may be used. After the silica precursors hydrolyze and silica-based particles are formed, the particles can be spherical and/or monodisperse.

One example version of the invention is an oil in water emulsion for forming silica-based particles. The emulsion includes an aqueous continuous phase; a dispersed phase comprising droplets including a non-polar material and/or one or more oils; and two different silica precursors, wherein the silica precursors can be templated on the droplets to form the silica-based particles. The emulsified droplets can initiate reaction of the silica precursors at interfaces between the dispersed droplets and the continuous phase.

The oil in water emulsion can include a surfactant selected from cationic, anionic, nonionic and amphoteric surfactants. The surfactant can be introduced to the emulsion below a critical micelle concentration of the surfactant for precursor interface interaction. A second surfactant can be introduced to the emulsion below a critical micelle concentration of the second surfactant for precursor interface interaction. The second surfactant can be selected from cationic, anionic, nonionic and amphoteric surfactants. The surfactant can be introduced to the emulsion above a critical micelle concentration of the surfactant, and a second surfactant can be introduced to the emulsion below a critical micelle concentration of the second surfactant for precursor interface interaction, wherein the second surfactant is selected from cationic, anionic, nonionic and amphoteric surfactants. The surfactant can be introduced to the emulsion above a critical micelle concentration of the surfactant, and a second surfactant can be introduced to the emulsion above a critical micelle concentration of the second surfactant for precursor interface interaction, wherein the second surfactant is selected from cationic, anionic, nonionic and amphoteric surfactants. The surfactant can be added above a critical micelle concentration of the surfactant to stabilize the particles and then diluted to reduce the level of surfactant to maintain the level below the critical micelle concentration of the surfactant before the precursors are added for precursor interaction.

Cationic surfactants may be especially beneficial when used in the method of the invention. The condensation reaction occurs at basic pH and therefore, any hydrolyzed silica precursor is deprotonated and therefore negative at basic pH. When a cationic surfactant is present at the dispersed phase-continuous phase interface, this drives the deprotonated hydrolyzed silica precursor to the interface thereby speeding up the reaction time. In addition, any positive charges on functional groups of the hydrolyzed silica precursor can drive further deprotonated hydrolyzed silica precursor to the interface thereby speeding up the reaction time.

At least one of the precursors can have multiple functionality. At least one of the precursors can have functional groups capable of preventing or limiting aggregation of the particles. At least one of the precursors can include a functional group that allows for attachment of a polymer or other molecular complex to a surface of the formed particles by covalent linking. At least one of the precursors can include a functional group having a net charge to attract towards an opposite charge of the surfactant at interfaces between the droplets and the continuous phase. The emulsion can have a charge associated with the surfactant to help speed up the reaction at interfaces between the droplets and the continuous phase by targeting and directing precursor formation at interfaces between the droplets and the continuous phase in a quicker fashion.

At least one of the silica precursors can include a functional group having a charge ratio to limit polar and non-polar penetrations through interfaces between the droplets and the continuous phase to allow better stabilization of the emulsion as well as assist in reactions. At least one of the precursors can include a combination of functional groups, and at least two of the combination of functional groups are selected from functional groups that allow for attachment of a polymer or other molecular complex to a surface of the particles by covalent linking, or functional groups having a net charge to attract towards an opposite charge of a surfactant at interfaces between the droplets and the continuous phase, and/or functional groups having a charge ratio to limit polar and non-polar penetrations through interfaces between the dispersed droplets and the continuous phase to allow better stabilization of the emulsion as well as assist in reactions.

A primary precursor of the two silica precursors can leave a first shell thickness of 1 nanometer to 500 nanometers, or 2 nanometer to 200 nanometers, or 2 nanometer to 100 nanometers, for the particle when the silica precursors are templated on a droplet. A secondary precursor of the two silica precursors can bond to the first shell to create an outer layer such that the first shell and the outer layer together have a thickness in the range of 1 nanometer to 1 micron.

The emulsion can include two or more oils which remain as a core of a silica particle shell after drying. At least one oil can remain in a silica particle shell after being washed.

Another example version of the invention is an emulsion templated silica particle formed from the oil in water emulsion. The silica particle can be modified from a continuously formed shell to a partially formed hollow shell by adjusting a ratio of two silica precursors in the emulsion. The weight ratio or the volume ratio of the first silica precursor to the second silica precursor can be from 1:99 to 99:1, or 1:50 to 50:1, or 1:25 to 25:1, or 1:5 to 15:1, or 1:1 to 10:1. If a third silica precursor is used, the second silica precursor and the third silica precursor can be added in a ratio from 1:99 to 99:1, or 1:50 to 50:1, or 1:25 to 25:1, or 1:5 to 15:1, or 1:1 to 10:1. Preferably, the silica precursors are different. The weight ratio or the volume ratio of the first silica precursor to the active ingredient can be from 1:99 to 99:1, or 1:50 to 50:1, or 1:25 to 25:1, or 1:5 to 15:1, or 1:10 to 10:1, or 1:100 to 5:1, or 1:10 to 5:1. The weight ratio or the volume ratio of the second silica precursor to the active ingredient can be from 1:99 to 99:1, or 1:50 to 50:1, or 1:25 to 25:1, or 1:5 to 15:1, or 1:10 to 10:1, or 1:100 to 5:1, or 1:10 to 5:1. If a third silica precursor is used, the second silica precursor and the third silica precursor can be added in a ratio from 1:99 to 99:1, or 1:50 to 50:1, or 1:25 to 25:1, or 1:5 to 15:1, or 1:1 to 10:1. The weight ratio or the volume ratio of the surfactant to the active ingredient can be from 1:99 to 99:1, or 1:50 to 50:1, or 1:25 to 25:1, or 1:5 to 15:1, or 1:10 to 10:1, or 1:100 to 5:1, or 1:10 to 1:1.

The templated silica particle may lose its internal core due to partial formation from a limited molar ratio of the two silica precursors. The silica particle may include a partially formed shell from aid of precursor hindrance. In one form, the silica particle allows for one or more particles of smaller size either with a pore or continuous shell to be present in the partially formed shell. The templated silica particle can have functional groups capable of attaching a coating by covalent bonding, non-covalent bonding, ionic bonding, electrostatic attraction, or any other attachment mechanism which allows for coating proximity within sub-nanometer ranges to 500 microns. The coating can be a polymeric material.

The templated silica particle can have multiple layering effects while trapping an active material inside layers. The templated silica particle can have 1 to 100 layers of silica deposited when the silica precursors are templated on a droplet. The particle can burst upon friction and release a payload contained within the particle. The particle can remain intact within environments of pH ranges from 0.01-14. The templated silica particle can be chemically altered and open for diffusion of a payload contained within the particle.

The templated silica particle can be formed from more than two precursors making a shell with a thickness of 1 nanometer to 5 microns. The templated silica can have an overall size of 10 nanometers to 250 microns. The templated silica particle can include an oil droplet having a size of 1 nanometer to 200 microns, or 800 nanometers to 80 microns. Preferably, the templated silica particle maintains a template volume of greater than 0.01%. Preferably, the particle maintains a template volume up to 100% loading. Preferably, the particle maintains greater than 0.01% of a loaded material if the loaded material dissipates or leaches from the particle. The templated silica particle allows for complete release of a payload material from the particle when the particle is intact or ruptured. In one form, the particle releases one layer of a loaded material at a time. In another form, the templated silica particle releases multiple layers of a loaded material at a time. The templated silica particle can release a loaded material due to coating dissociation. The particle can remain completely or partially intact due to a coating on the particle.

In one form, the templated silica particle has a zeta potential ranging from −80 mV to 150 mV. The zeta potential can be measured on a Zetasizer instrument from Malvern Instruments, Malvern, UK, or on a ZetaPlus or ZetaPALS instrument from Brookhaven Instruments, Holtsville, N.Y. In some embodiments, the templated silica particles have a zeta potential of at least about 5, 10, 12, 14, 16, 18, 20, 25, 30, 35, 40, 45, 50, 55, 60, 65, 70, 80, 90 or 100 mV. In some embodiments, the templated silica particles have a zeta potential of no more than about 15, 20, 25, 30, 35, 40, 45, 50, 55, 60, 65, 70, 80, 90, 100, or 150 mV. In some embodiments the zeta potential is between 10 and 70 mV, between 20 and 65 mV, between 25 and 65 mV, between 30 and 60 mV, between 30 and 100 mV, between 40 and 80 mV, between 70 and 100 mV or between 40 and 55 mV.

The templated silica particle can include an oil with a mixture of solids, semi solids, or other liquids or gases. The templated silica particle formed from the oil in water emulsion can have water soluble constituents mixed in an oil forming the emulsion for the templating.

Yet another example version of the invention is an oil in water emulsion for making silica-based particles. The emulsion includes an aqueous continuous phase; a dispersed phase comprising droplets including a non-polar material; and an organically modified silica precursor with at least one carbon, wherein the silica precursor can be templated on the droplets to make the silica-based particles. The organically modified silica precursor can include at least one carbon on two, three or all four bonding sites of silicon in the organically modified silica precursor. The organically modified silica precursor can include two or more of the same organically modified groups on bonding sites of the silicon in the organically modified silica precursor.

Still another example version of the invention is an oil-in-water emulsion system for making silica coated particles. The emulsion includes an aqueous continuous phase; a surfactant component comprising a surfactant selected from anionic surfactants, nonionic surfactants, cationic surfactants, nonionic surfactants, and mixtures thereof, each surfactant in the surfactant component being at or below a critical micelle concentration of each surfactant; a dispersed phase comprising one or more non-polar materials that are incompatible with the aqueous phase and form droplets; a first organically modified silica precursor having at least one carbon atom and having a first functional group that is capable of further reaction, and a second organically modified silica precursor having at least one carbon atom that is combined with the first organically modified silica precursor and having a second functional group, wherein the at least one carbon atom and the second functional group are in a ratio from 1 to 99 to 99 to 1, wherein the first organically modified silica precursor and the second organically modified silica precursor can be reacted to form precipitated silica shells around the droplets which act as templates. The first functional group can be selected from alcohols, amines, aldehydes, acids, esters, and groups including an unsaturated bond. The second functional group can be selected from alcohols, amines, aldehydes, acids, esters, and groups including an unsaturated bond. The aqueous phase can include a compound to control viscosity, wherein the compound is selected from water soluble polymers, salts, alcohols, glycols, alkylene ethoxylates, and mixtures thereof. The dispersed phase can include a compound to control viscosity, wherein the compound selected from oil soluble polymers, waxes, fatty alcohols, triglycerides, fatty acids, fatty amines, esters, hydrocarbons, and mixtures thereof.

A silica shell formed from this oil-in-water emulsion system can include an alcohol functional group on a surface of the silica shell that can be further reacted with: (i) an acid, an acid anhydride or an acid chloride to form an ester, or (ii) a hydrosilane that reacts to form a siloxy group that will link alkyl siloxane compounds to the shell surface, or (iii) a chlorosilane that reacts to form a siloxy group that will link alkyl siloxane compounds to the shell surface, or (iv) an epoxide that will react to form an ether group that will link alkyl groups (with or without additional functional groups) to the silica shell surface.

A silica shell formed from this oil-in-water emulsion system can include an amine functional group on a surface of the silica shell that can be further reacted with: (i) an acid, an acid anhydride or an acid chloride to form an amide, or (ii) an alkylhalide (or dimethyl sulfate or diethyl sulfate) to form a 2°, 3° amine or a quaternary ammonium salt that will link an alkyl group(s) (with or without additional functional groups) to the silica sphere surface, or (iii) an amine salt with an epoxide that will react to form a 2°, 3° ammonium salt or a quaternary ammonium salt group that will link alkyl group(s) (with or without additional functional groups) to the silica shell surface, or (iv) an aldehyde or a ketone that will react to form an imine or Schiff base compounds that will link alkyl groups (with or without additional functional groups) to the silica shell surface, or (v) an acid to form an ammonium salt on the silica sphere surface to impart a positive (cationic) charge to the silica sphere surface.

A silica shell formed from this oil-in-water emulsion system can include an aldehyde functional group on a surface of the silica shell that can be further reacted with: (i) an aldehyde, ketone or ester to form an aldol condensation product that will link alkyl groups (with or without additional functional groups) to the silica shell surface, or (ii) an amine to form an imine or Schiff base compounds that will link alkyl groups (with or without additional functional groups) to the silica shell surface.

A silica shell formed from this oil-in-water emulsion system can include an acid functional group on a surface of the silica shell that can be further reacted with: (i) an alcohol to form an ester that will link alkyl groups (with or without additional functional groups) to the silica shell surface, or (ii) an amine to form an amide that will link alkyl groups (with or without additional functional groups) to the silica shell surface, or (iii) an amine to form an ionic ammonium salt that will link alkyl groups (with or without additional functional groups) to the silica shell surface, or (iv) a base to form an ionized acid group that will impart a negative (anionic) charge to the silica sphere surface.

A silica shell formed from this oil-in-water emulsion system can include an ester functional group on a surface of the silica shell that can be further reacted with: (i) an alcohol (or acid) group as required to transesterify to form a new ester linkage that will join alkyl groups (with or without additional functional groups) to the silica shell surface, or (ii) an amine to form an amide that will link alkyl groups (with or without additional functional groups) to the silica shell surface.

A silica shell formed from this oil-in-water emulsion system can include an unsaturated functional group on a surface of the silica shell that can be further reacted with: (i) a hydrosilane that reacts to form an alkylsilane linkage that will join alkyl siloxane compounds to the shell surface, or (ii) an additional unsaturated compound (along with appropriate catalysts or reaction conditions) to polymerize thereby attaching a polymer (that may have additional functional groups) to the silica shell surface.

A silica shell formed from this oil-in-water emulsion system can include a polymer attached to the first functional group and/or the second functional group on a surface of the silica. Preferred polymers include polymers having one or more quaternary ammonium cations.

In one non-limiting example of the invention, an emulsion is formed by homogenizing a mixture of oil (e.g., fragrance as an active ingredient) and a surfactant solution using a homogenizer. This process usually runs from 10-60 minutes. Then an oil in water emulsion is formed with the desired oil droplet sizes. A certain volume of this emulsion is transferred to a reaction container for the emulsion templating reaction. Ammonium hydroxide is first added to the emulsion solution as a basic catalyst for the sol-gel reaction with stirring. A pH of 8-12, and preferably 9-11 is used. Then a first silica precursor is introduced for the preliminary silica shell formation around the surfactant stabilized oil droplets and the reaction solution is stirred for a time period of anywhere between 2-24 hours. After this step, a second silica precursor is introduced over 30-60 minutes under stirring for the thickening of the shell and then after some time the stirring is stopped and the reaction solution is allow to sit for up to 2 days depending on what shell thickness is desired for the hollow silica-based particles. Alternatively, the time periods for addition of the first silica precursor and the second silica precursor can overlap. Preferably, the first silica precursor and the second silica precursor are different. The silica particles formed can be modified from continuously formed hollow shells to partially formed hollow shells by adjusting a ratio of the two silica precursors in the emulsion.

After the reaction is completed, a small volume of the reaction solution is transferred into a vial for washing with water using a centrifuge for about 3 times. At the end of washing, this solution is used to prepare scanning electron microscope samples for investigation of the shell formation and size distribution. A vacuum filter with the appropriate membrane pore size are used to collect the silica-based shells dry for long term storage.

In the invention, a unique emulsion system is formed in the aqueous phase that stabilizes the emulsion, preventing the coalescence of the oil droplets while the organic silica precursor is reacting.

Active ingredients can be encapsulated within the hollow silica-based particles of the invention. The particles can be viewed as having two parts, the core and the shell. The core contains the active ingredient, while the shell surrounds and protects the core. The core materials used in the invention can be solid or liquid, and if liquid, can be, for example, in the form of a pure compound, solution, dispersion or emulsion. The shell material can be a silica-based shell. The shell can be made permeable, semi-permeable or impermeable. Permeable and semi-permeable shells can be used for release applications. A permeable shell can be a shell including one or more passageways that extend from an inner surface of the shell (which is around the core) and the outer surface of the shell. Semi-permeable shells can be made to be impermeable to the core material but permeable to low molecular-weight liquids and can be used to absorb substances from the environment and to release them again when brought into another medium. The impermeable shell encloses the core material. To release the content of the core material, the shell must be ruptured.

The ceramic shells are prepared by a sol-gel based process in which a silica precursor is used. There are many silica precursors which can used in the present invention. For example, the silica precursor can be a silicate (silicon acetate, silicic acid or salts thereof), a silsequioxanes or poly-silsequioxanes, silicon alkoxides (e.g. from silicon methoxide to silicon octadecyloxide), and functionalized alkoxides (such as ethyltrimethoxysilane, aminopropyltriethoxysilane, vinyltrimethoxysilane, diethyldiethoxysilane, diphenyldiethoxysilane, etc). Further specific examples of silica precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, phenyltriethoxysilane, octylpolysilsesquioxane and hexylpolysilsesquioxane. The silica precursor may include, for example, from one to four alkoxide groups each having from 1 or more oxygen atoms, and from 1 to 18 carbon atoms, more typically from 1 to 5 carbon atoms. The alkoxide groups may be replaced by one or more suitable functional groups. Examples of functional groups attached to silica precursors include alkyls, alcohols, amines (including quaternary amines), amides, aldehydes, acids, esters, and groups including an unsaturated bond. Thus, an organically modified silica precursor can be used. An organically modified silica precursor can be a silica precursor wherein one or two (out of four) of the alkoxysilane groups has been replaced by organic groups like alkyls, alcohols, amines, amides, aldehydes, acids, esters, and groups including an unsaturated bond. The silica precursor may be a polysiloxane having, for example, 2 to 100 repeat units and having one or more quaternary ammonium cations. The processing is based on the hydrolysis and condensation of the silica precursors. Water is thus typically used as the condensing agent.

Various surfactants can be used in the method of the invention. In order to form an oil-in-water emulsion of the invention, surfactants with an HLB value above about 8 are generally used. In some cases, multiple surfactants are used. Where there are multiple surfactants, the combined HLB of the surfactants is generally used. The HLB of the surfactant or surfactants is between, for example, 7 and 13, 8 and 12, 9 and 11, 9.5 and 10.5. In some embodiments, the HLB of the surfactants is 8, 8.5, 9, 9.5, 10, 10.5, 11, 11.5, or 12. Surfactants suitable for forming the oil-in-water emulsion include anionic, non-ionic, cationic, and zwitterionic surfactants. Non-limiting example surfactants include: anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps; cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions; nonionic: surfactants of the form $C_n(EO)_m$ where the alkane chain (C) length n is from 6 to 20 carbons and the average number of ethylene oxide (EO) groups m is from 2 to 80, ethoxylated cholesterol; zwitterionics and semipolars—N,N,N-trimethylaminodecanoimide, amine oxide surfactants with alkyl chain length from 8 to 18 carbons, dodecyldimethylammoniopropane-1-sulfate, dodecyldimethylammoniobutyrate, dodecyltrimethylene diammonium chloride), decylmethylsulfonediimine, dimethyleicosylammoniohexanoate and relatives of these zwitterionics and semipolars with alkyl chain lengths from 8 to 20.

Various non-polar active ingredients can be used in the invention depending on the final use for the silica-based particles. Non-limiting examples for the active ingredient include sunscreens, steroidal anti-inflammatory actives, analgesic actives, antifungals, antibacterials, antiparasitics, anti-virals, anti-allergenics, anti-cellulite additives, medicinal actives, skin rash, skin disease and dermatitis medications, insect repellant actives, antioxidants, hair growth promoter, hair growth inhibitor, hair bleaching agents, deodorant compounds, sunless tanning actives, skin lightening actives, anti-acne actives, anti-skin wrinkling actives, anti-skin aging actives, vitamins, nonsteroidal anti-inflammatory actives, anesthetic actives, anti-pruritic actives, antimicrobial actives, dental care agents, personal care agents, nutraceuticals, pharmaceuticals, fragrances, flavorings, antifouling agents, pesticides, lubricants, etchants, and mixtures and combinations thereof. In one example embodiment, the non-polar active ingredient is a fragrance. In another example embodiment, the non-polar active ingredient is a sunscreen.

The size of the silica-based particles formed is determined, at least in part, by the conditions of the reaction including the size of the original emulsion, and the conditions used for formation of the silica-based particles. A distribution of particle sizes can be obtained, or particles of a uniform size can be formed. The silica-based particles can also be fractionated into a desired size range after formation. Fractionation can be carried out by methods known in the art such as selective precipitation, or by using filters or sieves in order to pass a selected size range and retain the rest. The size of the silica-based particles can be modified in order to suit a particular application.

In some embodiments, the mean size of the silica-based particles is between 10 nanometers and 1 millimeter, between 10 nanometers and 1 µm, between 1 µm and 100 µm, between 10 µm and 50 µm, between 50 µm and 200 µm, or between 200 µm and 500 µm. In some embodiments, the mean size of the silica-based particles is between 1 nanometer and 10 nanometers, between 10 nanometers and 100 nanometers, between 100 nanometers and 1 µm, between 150 nanometers and 800 nanometers, between 1 µm and 5 µm, between 1 µm and 10 µm, between 5 µm and 10 µm, between 1 µm and 20 µm, between 10 µm and 20 µm, between 10 µm and 100 µm, between 100 µm and 1 millimeter, between 1 millimeter to 10 millimeters, or larger. In some embodiments, the mean size of the silica-based particles is within plus or minus 10% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 µm, 5 µm, 10 µm, 25 µm, 50 µm, 75 µm, 90 µm, 100 µm, 250 µm, 500 µm, 750 µm, 900 µm, 1 millimeter, or larger. In some embodiments, the mean size of the silica-based particles is within plus or minus 50% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 µm, 5 µm, 10 µm, 25 µm, 50 µm, 75 µm, 90 µm, 100 µm, 250 µm, 500 µm, 750 µm, 900 µm, 1 millimeter, or larger. In some embodiments, the silica-based particles are monodisperse.

Thus, the method uses multifunctional silanes for particle encapsulation. The silanes can include functional groups such as: (1) lipophilic: aryls (e.g., phenyl); alkyls (e.g., behenyl, octyl, dodecyl, cetyl, stearyl, $C_{12}$-$C_{24}$ alkyl); (2) vinyl (e.g., acrylic acid); and (3) hydrophilic (e.g., polyethylene glycol, long chain alkylamine, carboxylates). The hollow shell layering can be controlled by the functional groups (such as phenyl and amine) that can block the encapsulation reaction, i.e., the thickness is varied by blocking groups that stop the reaction. Also, functional groups (such as phenyl) can align at the continuous phase/dispersed phase interface and form pores, i.e., the porosity is controlled by the functionalized silanes. In addition, varying ratios of secondary silanes can stop the encapsulation reaction (to form thinner walls), or make the particles cationic, or make the particles hydrophobic, and can control thicknesses of the walls of the particles (e.g., 2-60 nm). Three secondary silanes can also be beneficial (e.g., two cationics for net charge −0-80 mV zeta) for controlling reaction, or making cationic, or making hydrophobic.

The invention is further illustrated in the following Examples which are presented for purposes of illustration and not of limitation.

EXAMPLES

Example 1

An emulsion was formed by homogenizing a mixture of 5% of oil fragrance and 0.2% of a surfactant solution of Triton™ X-100 non-ionic surfactant (Octylphenol Ethoxylate, R—$C_6H_4$—O—$(CH_2CH_2O)_x$—H where R=octyl (C8) and x=9.5 avg.) using a Polytron 3100 homogenizer. This process ran for 30 minutes. An oil in water emulsion was formed with the desired oil droplet sizes. A volume of 25 milliliters of this emulsion was transferred to a reaction container for an emulsion templating reaction. Ammonium hydroxide was first added at 2% to the emulsion solution as catalyst for the sol-gel reaction with stirring, then 1 milliliter of a first silica precursor, phenyltriethoxysilane, was introduced for the preliminary silica shell formation around the surfactant stabilized oil droplets and the reaction solution was stirred for a time period of 2 hours. After this step, 0.125 milliliters of a second silica precursor, tetramethoxysilane (TMOS), was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution.

FIG. 1 shows a first SEM image of silica-based particles formed using the emulsion templating reaction of the invention. Note in FIG. 1 how the dual precursor, oil in water emulsion of the invention produced silica-based particles in the range of 150-800 or 700-900 nanometers. In the SEM image of FIG. 1, the presence of hollow particles having a continuously formed shell and hollow particles having a partially formed hollow shell can be seen. The formation of continuously formed shells or partially formed hollow shell can be adjusted by the ratio of the two silica precursors in the emulsion. Limited moles of silica precursor can provide monopore shells as shown in FIG. 1. Furthermore, in the SEM image of FIG. 1, the presence of a particle of smaller size within a pore of a larger shell can be seen.

Figure 2:
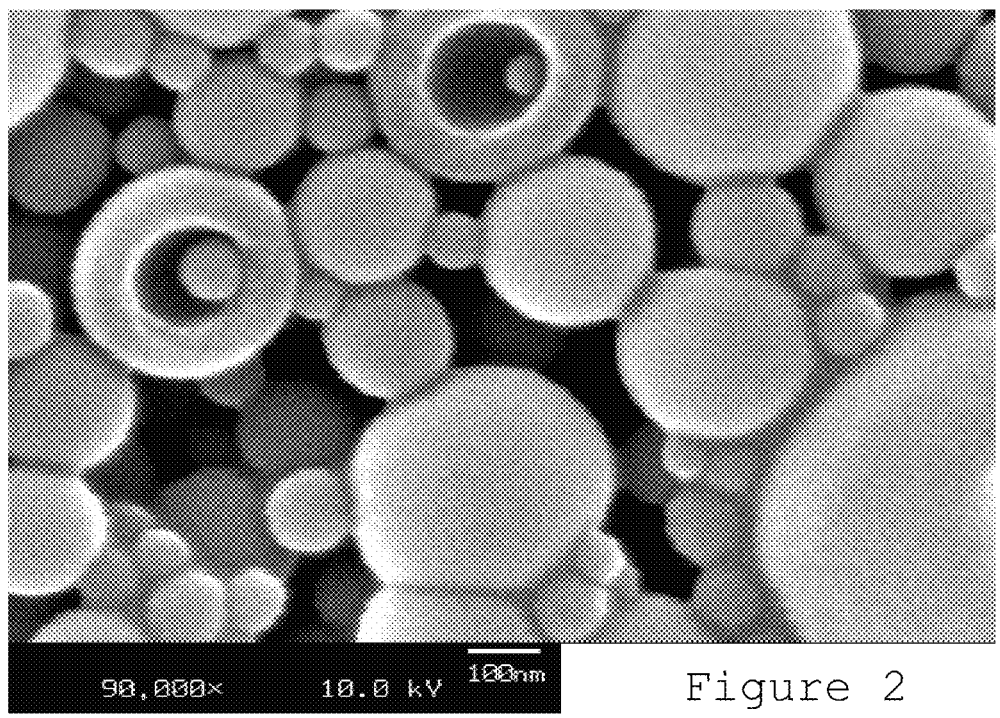
FIG. 2 is another SEM image of silica-based particles formed using a method of the invention.

FIG. 2 shows a second SEM image of silica-based particles formed using this method of the invention. In the SEM image of FIG. 2, the presence of a particle of smaller size within a pore of a larger shell can be seen. Without intending to be bound by theory, it is believed that the hydrophobic interior of the larger shell particle pulls the smaller particle into the pore of the larger particle. Alternatively, particles formed by the second silica precursor may form in the pore of the larger particle.

Figure 3:
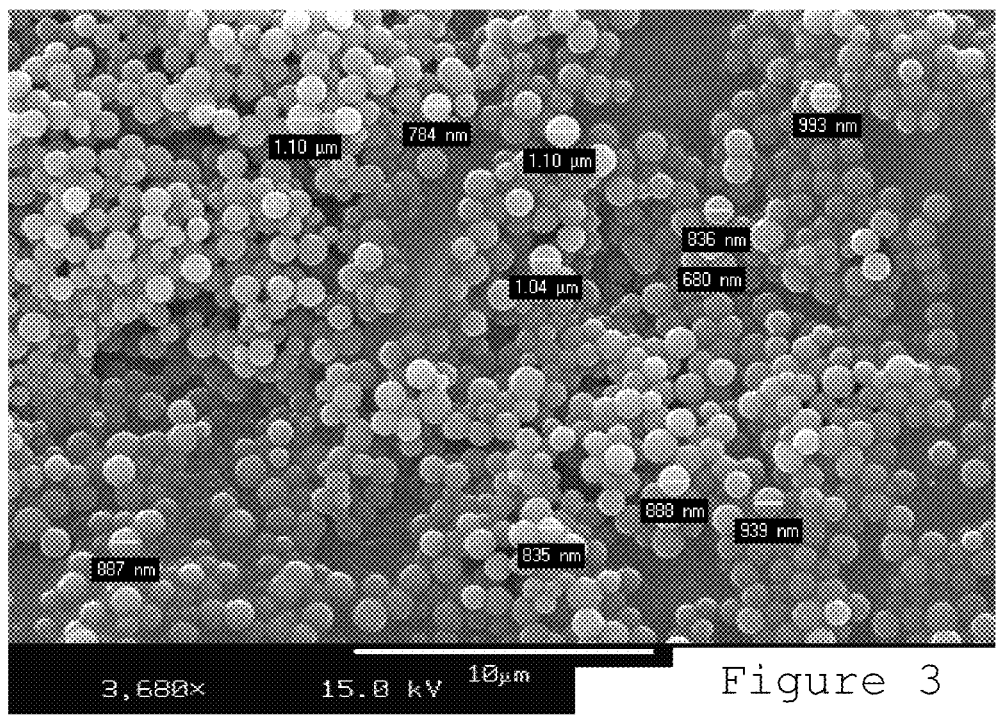
FIG. 3 is yet another SEM image of silica-based particles formed using a method of the invention.

FIG. 3 shows a third SEM image of silica-based particles formed using this method of the invention. In the SEM image of FIG. 3, the presence of particles of uniform size can be seen. Uniform particles having a size above 1 micron are present.

Figure 4:
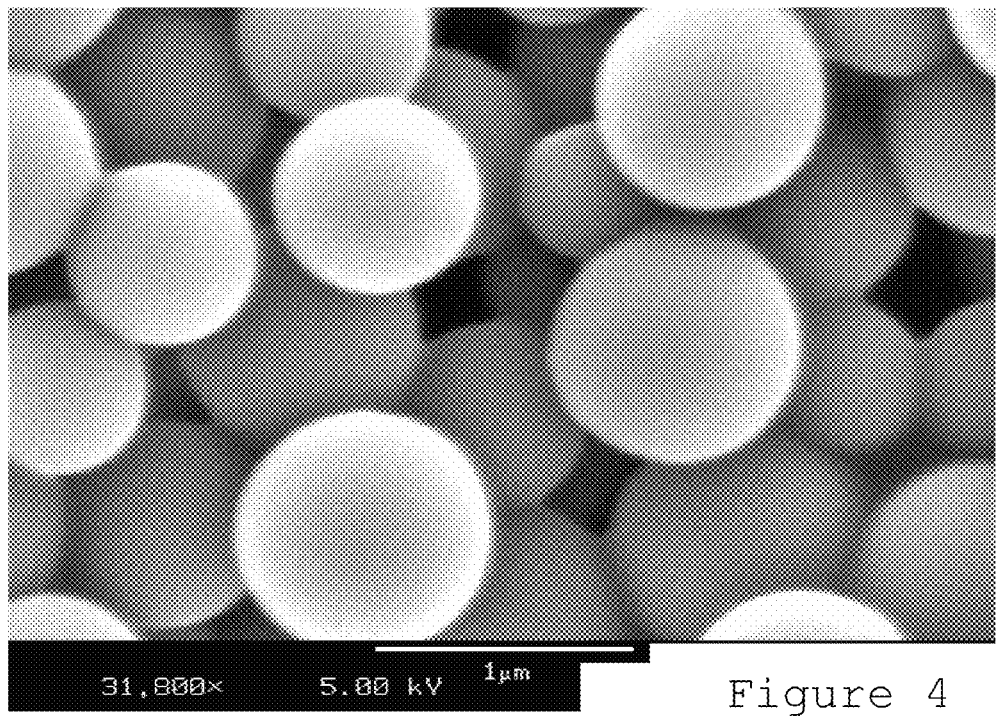
FIG. 4 is still another SEM image of silica-based particles formed using a method of the invention.

FIG. 4 shows a fourth SEM image of silica-based particles formed using this method of the invention. In the SEM image of FIG. 4, the particles are generally smooth. However, the small fuzziness on the particle surfaces is believed to be an indicator of the functional groups of the modified silica precursor on the surface. Also, certain particles in FIG. 4 show binding at contact areas which is an indication of covalent linking.

Figure 5:
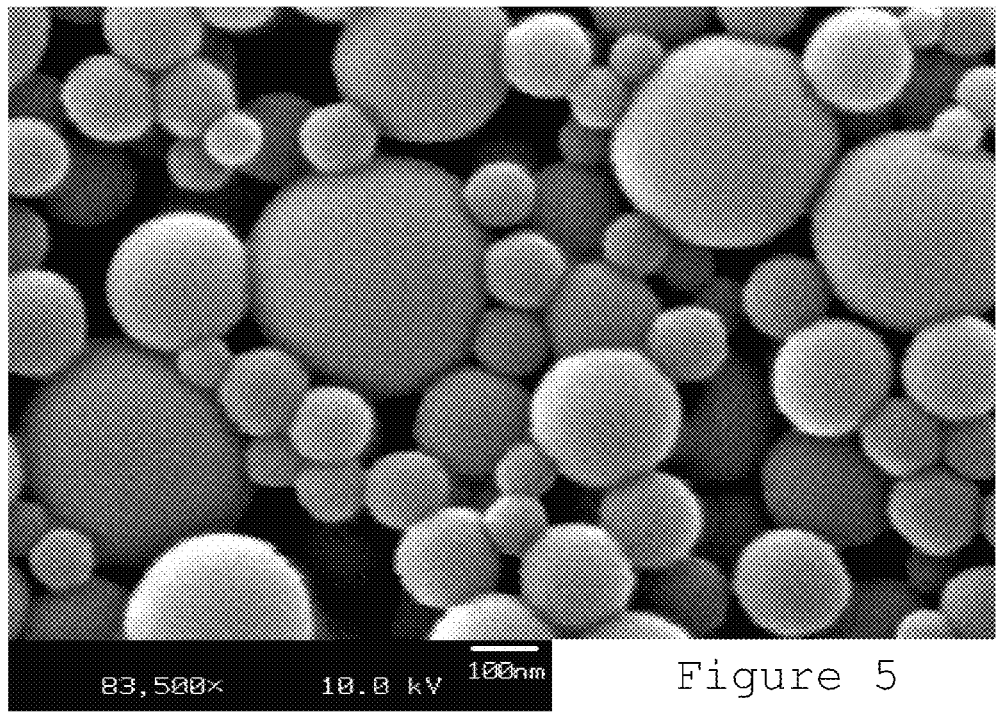
FIG. 5 is yet another SEM image of silica-based particles formed using a method of the invention.

FIG. 5 shows a fifth SEM image of silica-based particles formed using the method of the invention. In the SEM image of FIG. 5, the presence of spherical particles of a size below 100 nanometers can be seen. Also, a shell having a pore (i.e., a partially formed hollow shell) can be seen.

Figure 6:
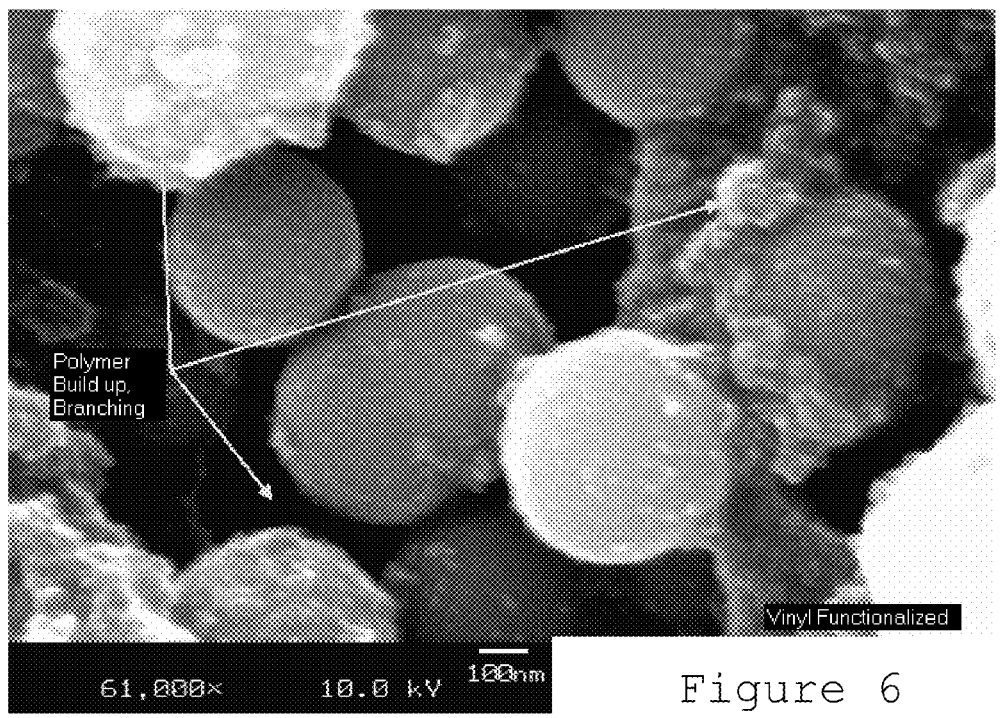
FIG. 6 is still another SEM image of silica-based particles formed using a method of the invention.

FIG. 6 shows a sixth SEM image of silica-based particles formed using this method of the invention wherein the aqueous phase included a water soluble polymer (e.g., polymethylmethacrylate). The roughened surface shown in FIG. 6 indicates polymer build up and branching between the vinyl functionalized surface of the shell of the particles. Thus, these particles have functional groups capable of attaching a coating by covalent bonding, non-covalent bonding, ionic bonding, electrostatic attraction, or any other attachment mechanism.

Example 2

An emulsion was formed by homogenizing a mixture of 0.75 grams of oil fragrance and 23.85 milliliters of water and 0.04 grams of a surfactant solution of Triton™ X-100 non-ionic surfactant (Octylphenol Ethoxylate, R—$C_6H_4$—O—$(CH_2CH_2O)_x$—H where R=octyl (C8) and x=9.5 avg.) using a Polytron 3100 homogenizer. This process ran for 30 minutes. An oil in water emulsion was formed with the desired oil droplet sizes. Ammonium hydroxide was added at 1.25 milliliters to the emulsion solution as basic catalyst for the sol-gel reaction with stirring, then 1.5 milliliters of a first silica precursor, phenyltriethoxysilane, was introduced for the preliminary silica shell formation around the surfactant stabilized oil droplets and the reaction solution was stirred for a time period of 2 hours. After this step, 0.125 milliliters of a second silica precursor, aminopropyltriethoxysilane, was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Very nice micron shells with minimal small ones were identified.

Example 3

An emulsion was formed by homogenizing a mixture of 0.5 grams of oil fragrance, 47.6 milliliters of water, 0.5 grams of a 10% solution of MERQUAT 550 (an aqueous solution of a highly charged cationic copolymer of 30 mole % diallyl dimethyl ammonium chloride and 70 mole % acrylamide), and 0.4 grams of a 10% surfactant solution of Triton™ X-100 non-ionic surfactant (Octylphenol Ethoxylate, R—$C_6H_4$—O—$(CH_2CH_2O)_x$—H where R=octyl ($C_8$) and x=9.5 avg.) using a Polytron 3100 homogenizer. This process ran for 30 minutes. An oil in water emulsion was formed with the desired oil droplet sizes. Ammonium hydroxide was added at 2.5 milliliters to the emulsion solution as basic catalyst for the sol-gel reaction with stirring, then 2.5 milliliters of phenyltriethoxysilane was introduced for the silica shell formation around the surfactant stabilized oil droplets and the reaction solution was stirred for a time period of 2 hours. The stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete shells were identified.

Thus, the invention provides a method for forming hollow silica-based particles suitable for containing one or more active ingredients or for containing other smaller particles which may include one or more active ingredients.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for forming silica-based particles, the method comprising the steps:
   (a) preparing an emulsion having a basic pH, the emulsion including a continuous phase that is polar and has one or more cationic surfactants, and a dispersed phase comprising droplets including a non-polar active ingredient and a non-polar diluent;
   (b) adding a first modified silica precursor to the emulsion such that the first modified silica precursor is emulsion templated onto the surface of the droplets to form a silica-based first shell layer around the droplets, wherein the first shell layer formed has a mean thickness of about 1 nm to about 500 nm within 2 hours from addition of the first modified silica precursor to the emulsion, and wherein the first modified silica precursor has the general formula (I):

   $$R^1_x\text{—Si—}(OR^2)_y \qquad (I)$$

wherein $R^1$ is selected from substituted and unsubstituted alkyl, aryl, alcohols, amines, amides, aldehydes, acids, esters, and functional groups having an unsaturated carbon-carbon bond, wherein $R^2$ is an alkyl group, wherein x+y=4, and wherein x=1 or 2;
   (c) adding a second modified silica precursor to the emulsion such that a coating can be deposited on at least part of the silica-based first shell layer through the interaction of the second modified silica precursor with the first modified silica precursor present in the silica-based first shell layer to form a second shell layer, wherein the first silica precursor and the second silica precursor are different; and
   (d) allowing the emulsion to sit for up to 2 days until the thickness of the the first shell layer and the second shell layer together have a mean thickness in the range of about 1 μm to about 250 μm;
   wherein the method produces silica-based particles having a silica-based shell surrounding a liquid core comprising the non-polar active ingredient and the non-polar diluent.

2. The method of claim 1, wherein the second modified silica precursor has the general formula (II):

$$R^3_m\text{—Si—}(OR^4)_n \qquad (II)$$

wherein $R^3$ is selected from substituted and unsubstituted alkyl, aryl, alcohols, amines, amides, aldehydes, acids, esters, and functional groups having an unsaturated carbon-carbon bond, and amino functional groups, wherein $R^4$ is an alkyl group, wherein m+n=4, and wherein m=1 or 2.

3. The method of claim 2, wherein at least one of $R^1$ of the first modified silica precursor and $R^3$ of the second modified silica precursor has a net charge to attract towards an opposite charge of a surfactant at interfaces between the droplets and the continuous phase.

4. The method of claim 2, wherein at least one of $R^1$ of the first modified silica precursor and $R^3$ of the second modified silica precursor prevents or limits aggregation of the silica-based particles.

5. The method of claim 2, wherein at least one of $R^1$ of the first modified silica precursor and $R^3$ of the second modified silica precursor allows for attachment of a polymer or other molecular complex to a surface of the particles by covalent linking.

6. The method of claim 2, wherein step (c) comprises adjusting a ratio of the first modified silica precursor and the second modified silica precursor to modify the silica-based silica particle from a continuously formed shell to a partially formed shell.

7. The method of claim 1, wherein the amount of the one or more cationic surfactants is below a critical micelle concentration of the surfactant for precursor interface interaction.

8. The method of claim 1, wherein the amount of the one or more cationic surfactants is above a critical micelle concentration of the surfactant.

9. The method of claim 1, wherein the one or more cationic surfactants speed up the reaction at interfaces between the droplets and the continuous phase by targeting and directing precursor formation at interfaces between the droplets and the continuous phase.

10. The method of claim 1, wherein the silica-based first shell layer has a first shell layer thickness of about 2 nm to about 200 nm.

11. The method of claim 1, wherein the second precursor is a water soluble polymeric compound or an unsaturated compound, and the coating includes a polymer.

12. The method of claim 11, wherein the second precursor is a water soluble polymeric compound.

13. The method of claim 11, wherein $R^1$ of the first modified silica precursor allows for attachment of the water soluble polymeric compound or the unsaturated compound to a surface of the particles by covalent linking.

14. The method of claim 1, wherein the non-polar active ingredient is an oil, and the method further comprises washing the silica-based particles such that the oil remains in the shell of the silica-based particles after being washed.

15. The method of claim 10, wherein the silica-based first shell layer has a first shell layer thickness of about 2 nm to about 100 nm.

16. The method of claim 1, wherein the silica-based particles have a Zeta potential range from 0 mV to 150 mV.

17. The method of claim 1, wherein the liquid core comprises the hydrophobic active ingredient in the form of a solution, dispersion, or emulsion.

18. The method of claim 1, wherein the shell is a mono-pore shell.

19. The method of claim 1, wherein the non-polar active ingredient includes a sunscreen, a steroidal anti-inflammatory active, an analgesic, active, an antifungal, an antibacterial, an antiparasitic, an antiviral, an anti-allergenic, an anti-cellulite additive, a medicinal active, a skin rash medication, a skin disease medication, a dermatitis medication, an insect repellant active, an antioxidant, a hair growth promoter, a hair growth inhibitor, a hair bleaching agent, a deodorant compound, a sunless tanning active, a skin lightening active, an antiacne active, an anti-skin wrinkling active, an anti-skin aging active, a vitamin, a nonsteroidal anti-inflammatory active, an anesthetic active, an anti-pruritic active, an anti-microbial active, a dental care agent, a personal care agent, a nutraceutical, a pharmaceutical, a fragrance, a flavoring, a antifouling agent, a pesticide, a lubricant, an etchant, mixtures thereof or combinations thereof.

* * * * *